United States Patent [19]

Patton

[11] Patent Number: 4,532,352

[45] Date of Patent: Jul. 30, 1985

[54] SEPARATION OF ANILINE AND P-FLUOROANILINE

[75] Inventor: Jerry R. Patton, Ellisville, Mo.

[73] Assignee: Mallinckrodt, Inc., St. Louis, Mo.

[21] Appl. No.: 544,990

[22] Filed: Oct. 24, 1983

[51] Int. Cl.³ .................... C07C 85/26; C07C 85/24
[52] U.S. Cl. .................... 564/438; 564/412; 564/442
[58] Field of Search .................... 564/412, 438, 442

[56] References Cited

FOREIGN PATENT DOCUMENTS 11104   8/1962   Japan ................................. 564/438
808425  2/1959   United Kingdom ................ 564/438

OTHER PUBLICATIONS

Morrison et al., *Organic Chemistry* (3d ed., 1976) pp. 730–731.
Goetz et al., "Quantenchemische Untersuchung der Zusammenhänge von PE-, UV- und pKa-Daten bei Aromatischen Phosphinen und Aminen", Liebigs Ann. Chem. 1977 (556–564).
Marschner, "Korrelation Zwischen Photoelektronen und Elektronen-Spektren-IV", Tetrahedron vol. 31, pp. 2303–2308.

*Primary Examiner*—Charles F. Warren
*Assistant Examiner*—Harry B. Shubin
*Attorney, Agent, or Firm*—Bernard, Rothwell & Brown

[57] ABSTRACT

A process is disclosed for the separation of p-fluoroaniline from a mixture, containing aniline and p-fluoroaniline, by contacting the mixture with a mineral acid in the presence of an organic solvent. The corresponding salt of p-fluoro-aniline is insoluble and can easily be isolated by conventional means such as filtration. If desired, the isolated salt can be converted to p-fluoroaniline by reaction with a base.

14 Claims, No Drawings

SEPARATION OF ANILINE AND P-FLUOROANILINE

BACKGROUND OF THE INVENTION

This invention relates to the separation of p-fluoroaniline from a mixture containing p-fluoroaniline and other aromatic compounds. More specifically there is disclosed a process for the separation of p-fluoroaniline from a mixture containing p-fluoroaniline and aniline comprising contacting the mixture with a mineral acid, in the presence of a solvent, thereafter isolating the resultant salt of p-fluoroaniline from the reaction mixture and then contacting the isolated salt with a base, thereby converting the salt to p-fluoroaniline.

P-fluoroaniline is a well known intermediate in the preparation of dyestuffs, pesticides and pharmaceuticals. U.S. Pat. No. 2,884,458 discloses a process for the manufacture of p-fluoroaniline by catalytic hydrogenation of nitrobenzene in anhydrous hydrogen fluoride. In the catalytic hydrogenation process, large amounts of ordinary aniline accompany the p-fluoroaniline and are difficult to separate. Generally, from 25 to 50 percent or more of the aniline product is aniline and the balance of p-fluoroaniline. Unfortunately, this reference does not provide an efficient means of separation of the p-fluoroaniline.

One method of separating aniline from p-fluoroaniline is disclosed in U.S. Pat. No. 3,639,482 and U.S. Pat. No. 3,580,951. U.S. Pat. No. 3,639,482 discloses a process for preparing fluoroaniline by heating at a temperature of from 100° to 230° C. under a pressure of 15 to 1500 p.s.i.a., a mixture of anhydrous hydrogen fluoride, nitrobenzene and a catalyst mixture consisting essentially of a compound selected from the group of palladium halides, rhodium halides, palladium oxides, and rhodium oxides and mixtures thereof, with an oxide of an element selected from the group of vanadium, molybdenum, tungsten, niobium, chromium, tantalum and mixtures thereof. After the reaction is completed, the product is isolated in a conventional manner. For example, the catalyst is removed by filtration and any excess hydrogen fluoride is evaporated or distilled off. Water is added and the aqueous layer is made alkaline. The liberated anilines are then separated and/or extracted with any suitable water immiscible organic solvent, for example, ether. The extract is dried and distilled to recover the fluoroaniline product. U.S. Pat. No. 3,580,951 describes the separation of the p-fluoroaniline from aniline in essentially the same manner as disclosed in U.S. Pat. No. 3,639,482.

U.S. Pat. No. 3,558,707 discloses a process for preparing fluoroanilines. The fluoroanilines are prepared by the deoxygenation and hydrofluorination of the corresponding nitrobenzenes which are reacted in anhydrous hydrogen fluoride at 0° to 230° C. under pressures of from 15 to 1500 p.s.i.a. in the presence of certain deoxygenating agents containing phosphorous or sulfur. After the reaction is completed, the fluoroaniline product is isolated in a conventional manner. For example, excess hydrogen fluoride is evaporated or distilled off. Water is added and the oxidation product together with unconverted deoxygenating agent, both of which are usually insoluble in water, are filtered off or otherwise separated. The aqueous layer is made alkaline and the liberated anilines are separated and/or extracted with any suitable water immiscible organic solvent, for example, ether. The extract is dried and distilled to recover the fluoroaniline product.

All of the prior art methods described above rely on fractional distillation to separate anilines from the corresponding fluoroanilines. Unfortunately, at atmospheric pressures aniline and p-fluoroaniline boil within about 3° C. of each other, which makes fractional distillation very difficult. Accordingly, there exists a demand for an efficient means of separating p-fluoroaniline from mixtures containing p-fluoroaniline and aniline.

SUMMARY OF THE INVENTION

The separation procedure of this invention is based on the fact that p-fluoroaniline forms mineral acid salts which are essentially insoluble in certain organic solvents, whereas aniline does not form corresponding salts in significant amounts. Accordingly, there is provided a process for the separation of p-fluoroaniline from a mixture containing p-fluoroaniline and aniline comprising:
 (a) contacting said mixture with a mineral acid, in the presence of an organic solvent to form an insoluble salt of p-fluoroaniline;
 (b) isolating the insoluble salt of p-fluoroaniline from the reaction mixture; and optionally
 (c) contacting said salt with a base thereby converting said salt to p-fluoroaniline.

DETAILED DESCRIPTION OF PREFERRED EMBODIMENTS

According to the present invention, there is provided a process for the separation of p-fluoroaniline from a mixture containing p-fluoroaniline and aniline.

The amount of p-fluoroaniline and aniline in the mixture can vary over wide limits but in general about 80% to about 95% by weight of the mixture will be p-fluoroaniline, with the remainder being aniline.

While the process of the invention can, if desired, be carried out in a batch-wise manner, it is preferable that it be carried out in a continuous manner. In accordance with the preferred embodiment, the mineral acid and the mixture containing the p-fluoroaniline and aniline are continuously added to a reactor containing a suitable solvent, whereupon the p-fluoroaniline reacts with the mineral acid to form an insoluble salt. The p-fluoroaniline salt is then separated by filtration and the solvent is recycled. Over a period of time, aniline accumulates in the recycled solvent. When the accumulated aniline reduces the p-fluoroaniline/aniline mixture in the reactor to less than about 80% p-fluoroaniline, the aniline must be removed from the solvent. If this is not done, small but significant amounts of mineral acid salts of aniline will contaminate the p-fluoroaniline salts which are formed. Accumulated aniline can be removed by stripping off the solvent in a conventional manner and the solvent can then be reused in the process.

For the purposes of this invention, mineral acids are meant to include concentrated or dilute solutions of hydrochloric acid, sulfuric acid, phosphoric acid, hydrobromic acid and nitric acid. Especially preferred is hydrochloric acid. The amount of mineral acid needed is at least the amount required stoichiometrically to react with the p-fluoroaniline to form the corresponding salt thereof. Excess amounts of mineral acid generally will not have any undesirable effects.

The reaction can be carried out in a conventional reaction vessel. Preferably the reaction vessel is a closed vessel equipped with a means for stirring, a thermometer, condenser, means for controlling the temperature of the reaction mixture as well as a means for introducing the mineral acid.

The conditions for the reaction between the mineral acid and the mixture of aniline and p-fluoroaniline should be such that there is a complete reaction of all the p-fluoroaniline. Since the mineral acid salt forms almost immediately upon contact between the p-fluoroaniline and the mineral acid, reaction time is not critical. Typical reaction temperatures are from 0° to 75° C. and preferably from 10° C. to 40° C. Suitable reaction pressures are from 0 to 1,000 p.s.i.g., and preferably from 0 to 50 p.s.i.g.

The reaction between the p-fluoroaniline and the mineral acid is carried out in the presence of an organic solvent in which the mineral acid salt of p-fluoroaniline is insoluble. Suitable solvents include ethyl acetate, heptane, hexane, methylene chloride or mixtures thereof. The amount of solvent is not critical and can be any amount which provides suitable contact of the reactants and allows ease of handling.

As a result of the above reaction, the p-fluoroaniline forms its corresponding salt which is insoluble in the reaction solvent. Consequently, the salt can be separated from the solution containing the aniline by conventional means, such as, for example, filtration.

The isolated salt of fluoroaniline can be contacted with an aqueous base to convert the salt to p-fluoroaniline. Suitable aqueous bases include, for example, hydroxides such as sodium hydroxide, potassium hydroxide, calcium hydroxide and ammonium hydroxide; carbonates such as sodium carbonate and potassium carbonate; and oxides such as calcium oxide and barium oxide. The p-fluoroaniline salt and the base are reacted in stoichometric amounts, typically from about 1.0 to about 1.5 mole of base per mole of p-fluoroaniline salt. Preferably from 1.0 to 1.1 molar equivalents of base are used.

When the salt is contacted with a base, suitable conditions can be from 0° to about 60° C. preferably about 10° C. to about 24° C. and a pressure about 0 p.s.i.g. preferably about 0 to about 5 p.s.i.g.

In the following examples, all percentages are based on weight unless stated to the contrary.

The following examples are supplied in order to illustrate, but not necessarily to limit, the process of the present invention.

EXAMPLE 1

A three liter, three necked flask was equipped with a stirrer, condenser, and a gas inlet below the liquid surface. A 300 gram mixture containing 14% by weight aniline and 86% p-fluoroaniline was charged into the flask. Thereafter, 1.5 liters of heptane and 300 ml of ethyl acetate was charged into the vessel. The reactants were stirred as anhydrous HCl was bubbled into the mixture through the gas inlet. After excess hydrogen chloride (gas) had been added, the mixture was filtered to give 350 grams of white p-fluoroaniline hydrochloride salts. The filtered heptane solution was found to contain no p-fluoroaniline and the salts were greater than 97% p-fluoroaniline hydrochloride.

EXAMPLE 2

Into a vessel similar to that used in example 1 was charged 400 grams of a mixture containing 95.5% by weight of p-fluoroaniline and 4.5% by weight of aniline. Two liters of ethyl acetate were then charged to the aniline mixture and the mixture was stirred. Thereafter, anhydrous hydrogen chloride was bubbled in below the liquid surface. Samples of the hydrochloride salts were taken after two hours, three hours and after an excess of HCl had been added. The samples of the salts were then placed in deionized water, and were made basic with potassium hydroxide. The samples were then distilled to give 250 grams (99.7% p-fluoroaniline) for sample 1, sample 2 resulted in 100 grams (97% by weight p-fluoroaniline) and sample 3 resulted in 50 grams (85% p-fluoroaniline).

EXAMPLE 3

To the same type of vessel used in the previous examples was charged 400 grams of a mixture containing 85% by weight p-fluoroaniline and 15% by weight of aniline. Thereafter, two liters of methylene chloride were charged to the vessel and the mixture was stirred. Thereafter, anhydrous hydrogen chloride was bubbled in the mixture until 70% of the p-fluoroaniline had been removed as the hydrochloride salt. The purity of the salt was found to be in excess of 95% p-fluoroaniline with the remaining material in the vessel being 65% by weight p-fluoroaniline and 35% by weight aniline.

While certain embodiments and details have been shown for the purpose of illustrating the invention, it will be apparent to those skilled in the art that various changes and modifications may be made therein without departing from the scope of the invention.

I claim:

1. A process for the separation of p-fluoroaniline from a mixture containing p-fluoroaniline comprising:
   (a) contacting said mixture with a mineral acid in the presence of an organic solvent to form an insoluble salt of p-fluoroaniline;
   (b) isolating the insoluble salt of p-fluoroaniline from the reaction mixture.

2. A process for the separation of p-fluoroaniline from a mixture containing p-fluoroaniline and aniline comprising:
   (a) contacting said mixture with a mineral acid, in the presence of a solvent selected from the group consisting of ethyl acetate, heptane, hexane, methylene chloride or mixtures thereof to form an insoluble salt of p-fluoroaniline;
   (b) isolating the insoluble salt of p-fluoroaniline from the reaction mixture.

3. The process of claim 1 wherein said mineral acid is selected from the group of hydrochloric acid, sulfuric acid, phosphoric acid, hydrobromic acid and nitric acid.

4. The process of claim 3 wherein said mineral acid is hydrochloric.

5. The process of claim 1 wherein there is present at least a stoichiometric equivalent of mineral acid to p-fluoroaniline present in the mixture.

6. The process of claim 1 wherein said solvent is methylene chloride.

7. The process of claim 1 wherein said solvent is ethyl acetate.

8. The process of claim 1 wherein said solvent is heptane.

9. The process of claim 1 wherein said solvent is hexane.

10. The process of claim 1 wherein said solvent is a mixture of heptane and ethyl acetate.

11. The process of claim 1 wherein said isolated salt of p-fluoroaniline is contacted with a base to convert it to p-fluoroaniline.

12. The process of claim 11 wherein said base is selected from the group comprising aqueous solutions of sodium hydroxide, potassium hydroxide, calcium hydroxide, sodium carbonate, potassium carbonate, calcium oxide and barium oxide.

13. The process of claim 12 wherein said base is potassium hydroxide.

14. The process of claim 11 wherein there is added at least a stoichiometric equivalent of base to the amount of p-fluoroaniline salt present in the reaction mixture.

* * * * *